US011751847B2

(12) United States Patent
Daloz et al.

(10) Patent No.: US 11,751,847 B2
(45) Date of Patent: Sep. 12, 2023

(54) ULTRASOUND TRANSDUCER AND METHOD FOR WAFER LEVEL BACK FACE ATTACHMENT

(71) Applicant: General Electric Healthcare, Schenectady, NY (US)

(72) Inventors: Flavien Daloz, Antibes (FR); Jason Barrett, Queen Creek, AZ (US); Edouard Da Cruz, Nice (FR); Jean Pierre Malacrida, Saint Laurent (FR)

(73) Assignee: GE PRECISION HEALTHCARE LLC, Milwaukee, WI (US)

( * ) Notice: Subject to any disclaimer, the term of this patent is extended or adjusted under 35 U.S.C. 154(b) by 855 days.

(21) Appl. No.: 16/703,406

(22) Filed: Dec. 4, 2019

(65) Prior Publication Data

US 2020/0107814 A1 Apr. 9, 2020

Related U.S. Application Data

(62) Division of application No. 15/385,671, filed on Dec. 20, 2016, now Pat. No. 10,561,398.

(51) Int. Cl.
| | |
|---|---|
| *A61B 8/00* | (2006.01) |
| *H10N 30/073* | (2023.01) |
| *H10N 30/088* | (2023.01) |
| *H10N 30/00* | (2023.01) |
| *B06B 1/06* | (2006.01) |

(52) U.S. Cl.
CPC .......... *A61B 8/4483* (2013.01); *B06B 1/0644* (2013.01); *H10N 30/073* (2023.02); *H10N 30/088* (2023.02); *H10N 30/10516* (2023.02)

(58) Field of Classification Search
CPC .. H01L 41/0815; H01L 41/313; H01L 41/338
See application file for complete search history.

(56) References Cited

U.S. PATENT DOCUMENTS

| | | | |
|---|---|---|---|
| 7,905,007 B2 | 3/2011 | Calisti et al. | |
| 2003/0007038 A1* | 1/2003 | Nakatani | B41J 2/1623 347/72 |
| 2004/0051423 A1* | 3/2004 | Florian | H01L 41/083 310/328 |
| 2006/0025690 A1* | 2/2006 | Guigne | G01S 15/8936 600/447 |
| 2009/0182233 A1 | 7/2009 | Wodnicki | |
| 2010/0020645 A1* | 1/2010 | Wodnicki | G10K 11/004 367/155 |
| 2010/0066207 A1* | 3/2010 | Saito | A61B 8/4281 310/335 |
| 2011/0181149 A1 | 7/2011 | Shikata | |
| 2011/0316387 A1* | 12/2011 | Togasaki | B06B 1/0622 310/334 |
| 2012/0157853 A1 | 6/2012 | Gelly et al. | |

(Continued)

*Primary Examiner* — Peter Dungba Vo
*Assistant Examiner* — Jose K Abraham
(74) *Attorney, Agent, or Firm* — McCoy Russell LLP

(57) ABSTRACT

Methods and systems are provided for a single element ultrasound transducer. In one embodiment, the ultrasound transducer comprises a front face, a back face parallel to the front face, a piezoelectric layer having a top surface electrically coupled to the signal pad and a bottom surface electrically coupled to the ground pad. In this way, the transducer can work robustly and may be automatically mounted to an imaging probe.

18 Claims, 10 Drawing Sheets

(56) References Cited

U.S. PATENT DOCUMENTS

| | | | |
|---|---|---|---|
| 2014/0103782 A1* | 4/2014 | Togasaki | H01L 41/22 |
| | | | 29/25.35 |
| 2014/0132114 A1 | 5/2014 | Fukase et al. | |
| 2014/0375171 A1 | 12/2014 | Tai | |
| 2015/0266059 A1 | 9/2015 | Kubo et al. | |
| 2016/0192081 A1* | 6/2016 | Horii | H04R 1/028 |
| | | | 379/420.02 |
| 2018/0169701 A1 | 6/2018 | Daloz et al. | |

* cited by examiner

ULTRASOUND TRANSDUCER AND METHOD FOR WAFER LEVEL BACK FACE ATTACHMENT

CROSS-REFERENCE TO RELATED APPLICATIONS

This application is a divisional of U.S. patent application Ser. No. 15/385,671, entitled "ULTRASOUND TRANSDUCER AND METHOD FOR WAFER LEVEL FRONT FACE ATTACHMENT," and filed on Dec. 20, 2016. The entirety of the above-identified application is hereby incorporated by reference for all purposes.

FIELD

Embodiments of the subject matter disclosed herein relate to an ultrasound transducer, and more particularly, to a single element ultrasound transducer with wafer level back face attachment.

BACKGROUND

Single element transducers can be mounted to a distal end of a probe for invasive imaging of blood vessels or cavities within the human body. By sending a voltage signal to the two electrodes of the transducer, a piezoelectric material within the transducer is excited and generates acoustic signals. The same piezoelectric material can also convert acoustic signals reflected from an object into voltage signals. The transducer may be assembled to a cable to form a forward looking probe, that is, a probe for imaging in the same direction as the longitudinal axis of the cable. The forward looking probe can be used in applications such as rectal imaging. Alternatively, the transducer may be assembled to a cable to form a side looking probe. By rotating the side looking probe along its longitudinal axis, a plane perpendicular to the longitudinal axis of the probe can imaged. The side looking probe can be used in applications such as intravascular imaging. Multiple single element transducers may also be assembled into a sparse array (such as a basket type array) for applications such as mapping a heart chamber. Since the ultrasound probes are designed for invasive imaging, miniaturized ultrasound transducers may be utilized.

Wiring the two electrodes of the transducer to the cable can be challenging due to the small size of the transducer. One approach is to attach one electrode of the transducer to a substrate having a printed circuit, and manually apply silver epoxy to connect the other electrode to the substrate. However, this process lacks reproducibility and robustness. Since silver epoxy has high viscosity, it is difficult to manually apply a controlled amount of epoxy. Silver epoxy also lacks robust adhesion to the substrate due to its high sensitivity to moisture and long curing time. Further, due to long touch time and cycle time, the process is not suitable for manufacturing disposable probes.

BRIEF DESCRIPTION

In one embodiment, an ultrasound transducer comprises a front face, a back face parallel to the front face, and a flex attachment. The back face includes a signal pad, a ground pad, and a groove separating the signal pad from the ground pad. The flex attachment has a first conductive layer and a second conductive layer separated by a non-conductive layer. The first conductive layer of the flex attachment is electrically coupled to the signal pad and the second conductive layer of the flex attachment is electrically coupled to the ground pad. In this way, the two electrodes (the ground pad and the signal pad) of the transducer are integrated into the transducer body with wafer level packaging, and the transducer may be reliably coupled to the probe via the flex attachment. Further, such configuration enables fast and automatic coupling of the transducer with the cable of the probe.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

Figure 1:
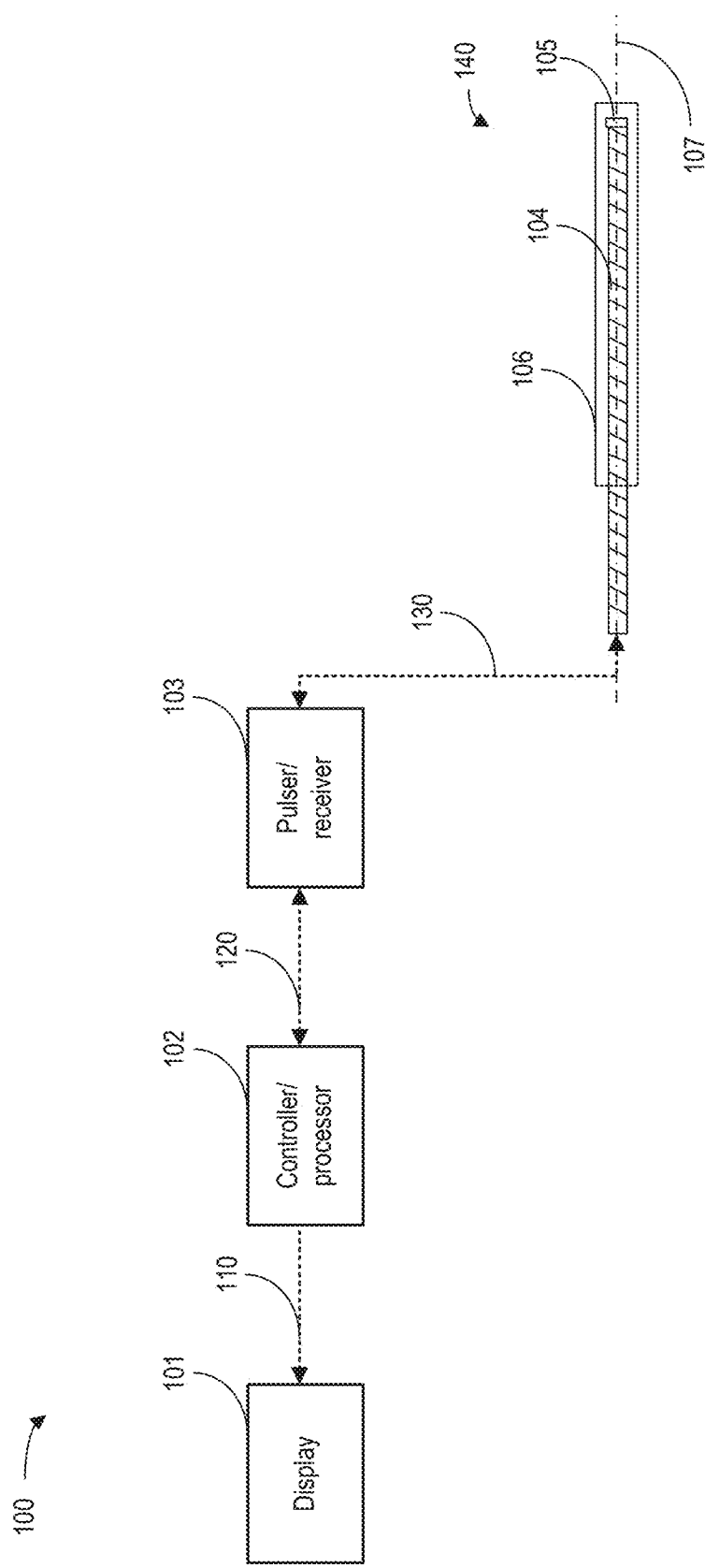
FIG. 1 shows an example ultrasound system attached to a probe including a single element ultrasound transducer.
Figure 3:
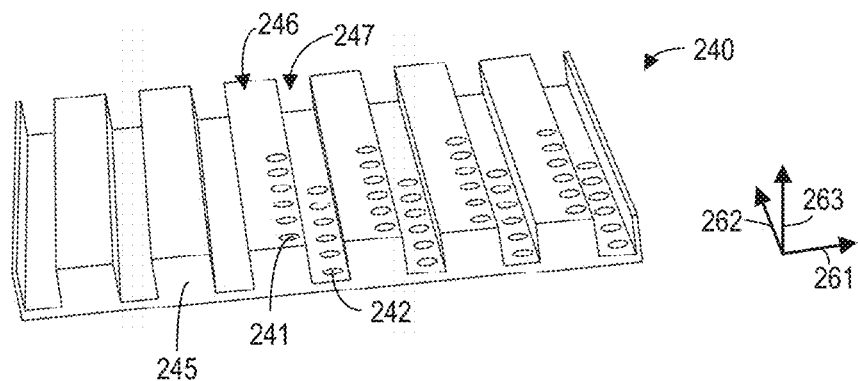
FIG. 3 shows a three dimensional rendering of the second comb structure of FIG. 2D.
Figure 4:
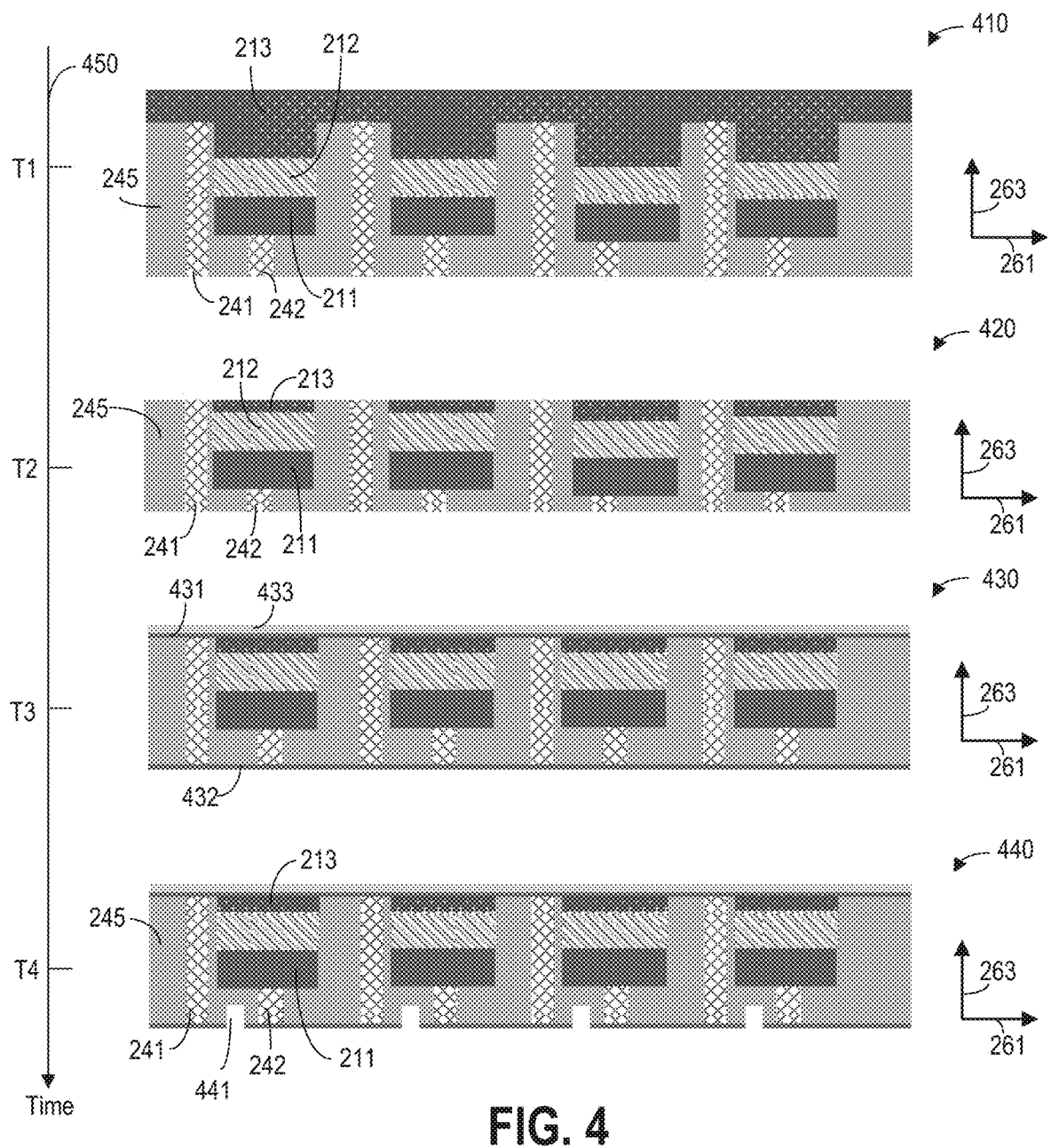
FIG. 4 illustrates a procedure for laminating the first and second comb structures of FIGS. 2B and 2D into an acoustic stack.
Figure 5A:
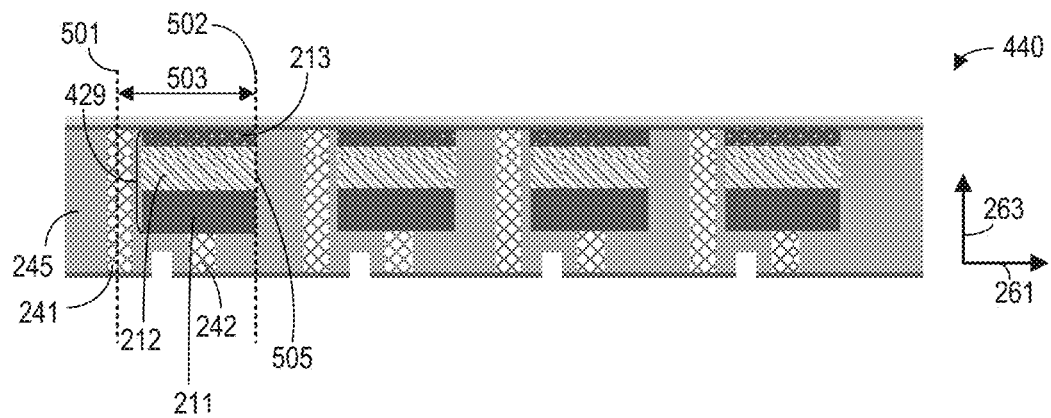
FIG. 5A shows lateral dicing lines for cutting the acoustic stack of FIG. 4 into individual single element ultrasound transducers.
Figure 5B:
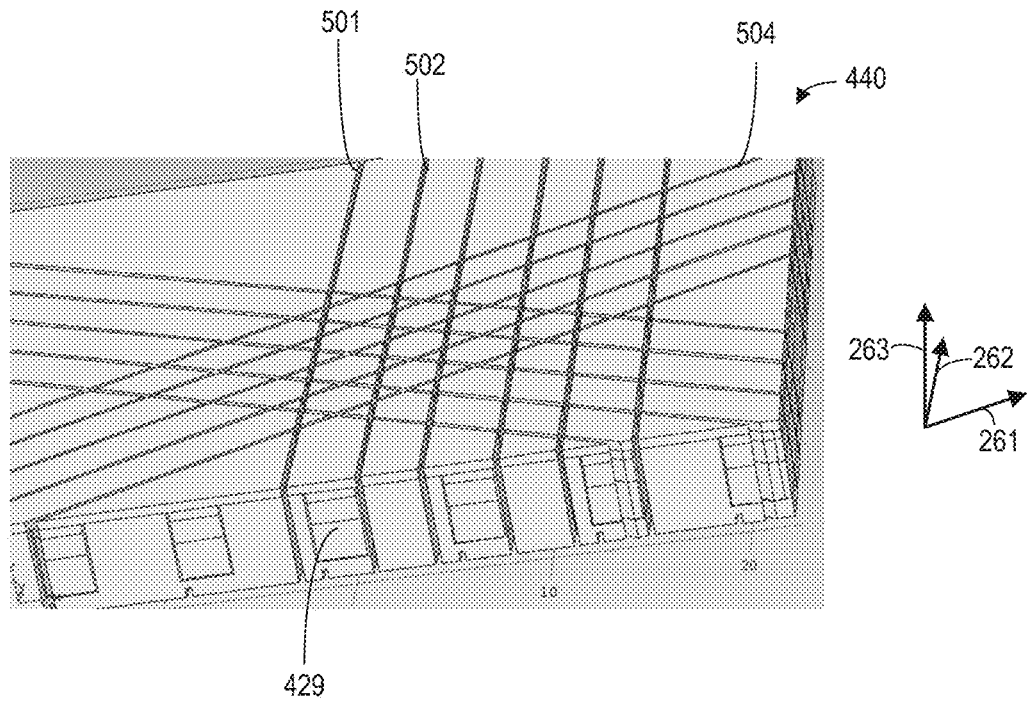
FIG. 5B illustrates lateral and diagonal dicing lines for cutting the acoustic stack of FIG. 4 into individual single element ultrasound transducers.
Figure 7A:
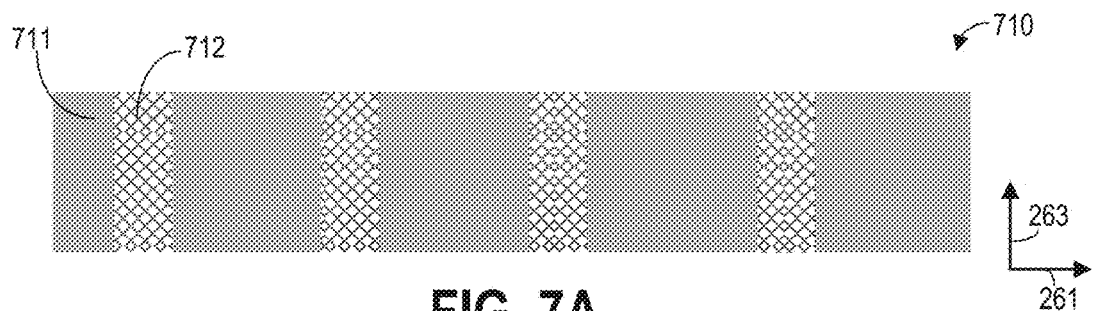
FIG. 7A shows a substrate with conductive base package.
Figure 7B:
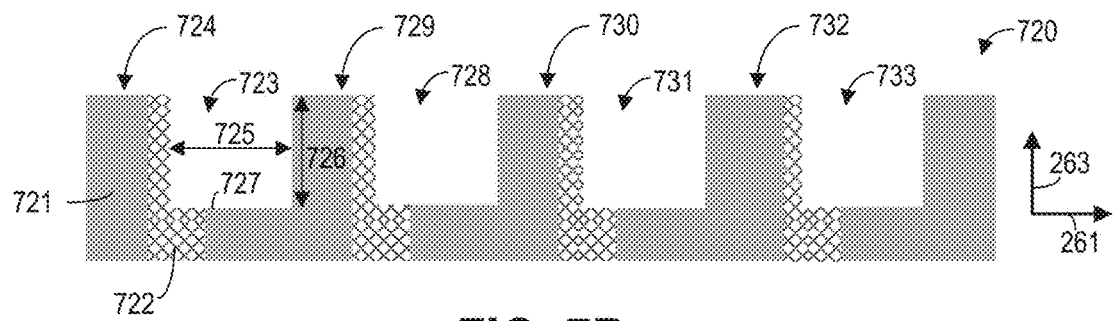
FIG. 7B shows another embodiment of a second comb structure.
Figure 8:
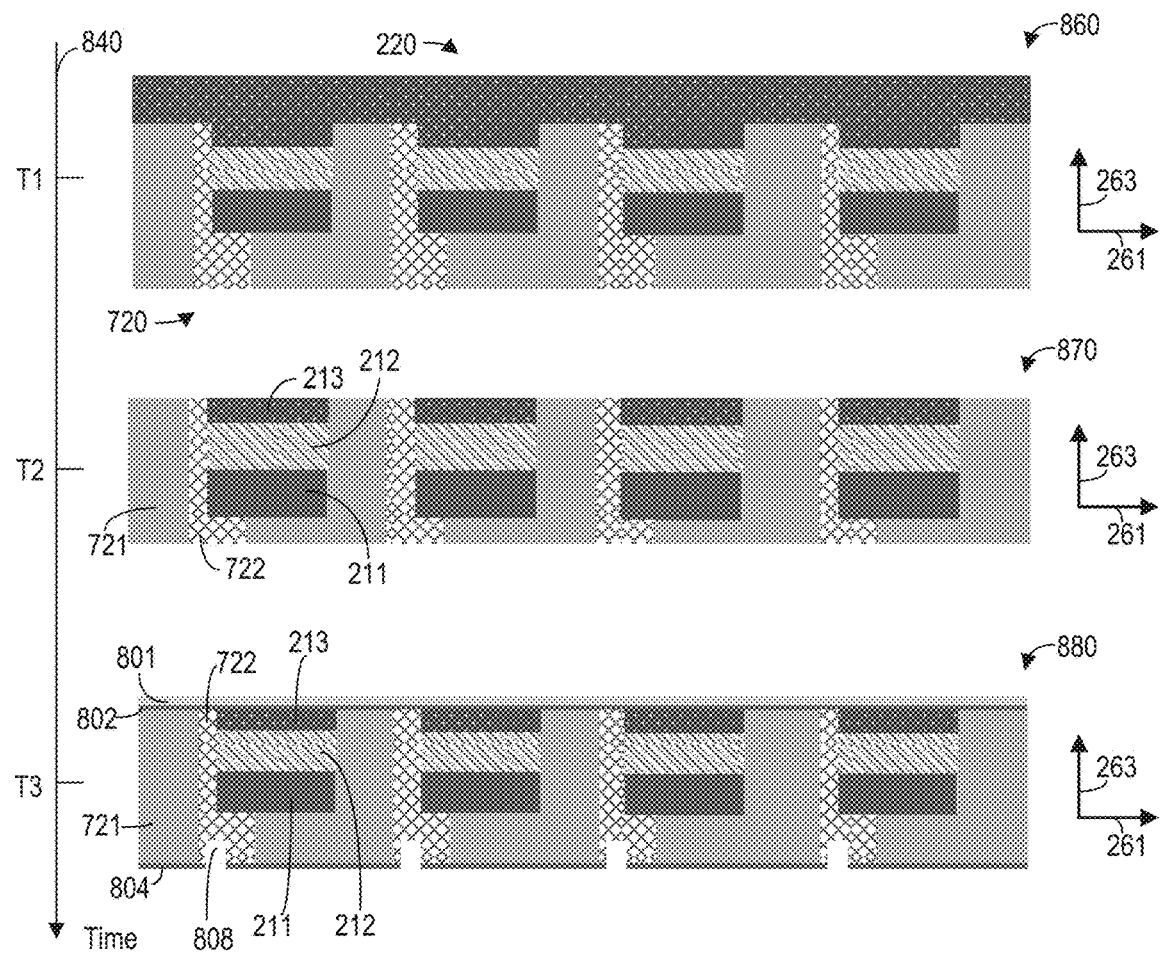
FIG. 8 shows the procedure of manufacturing an acoustic stack based on the second comb structure of FIG. 7B.
Figure 9:
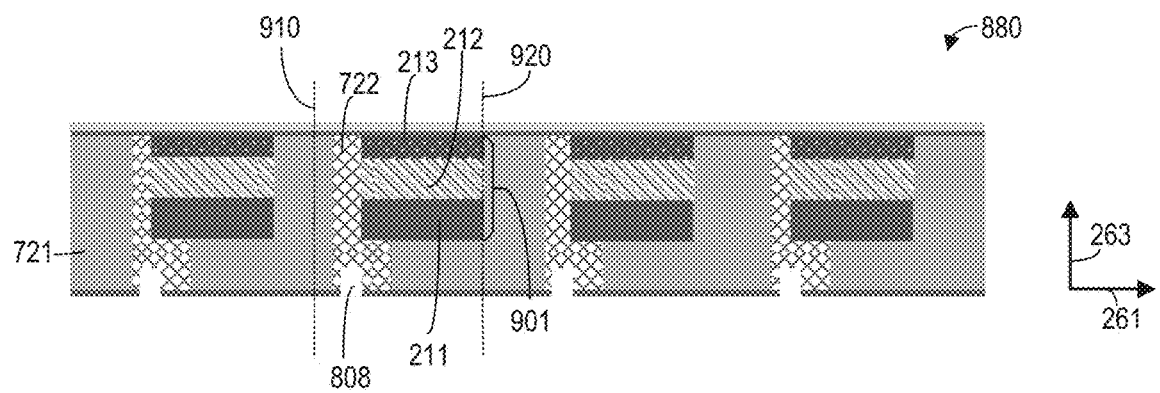
FIG. 9 shows lateral dicing lines for manufacturing a second embodiment of a transducer.
Figure 10A:
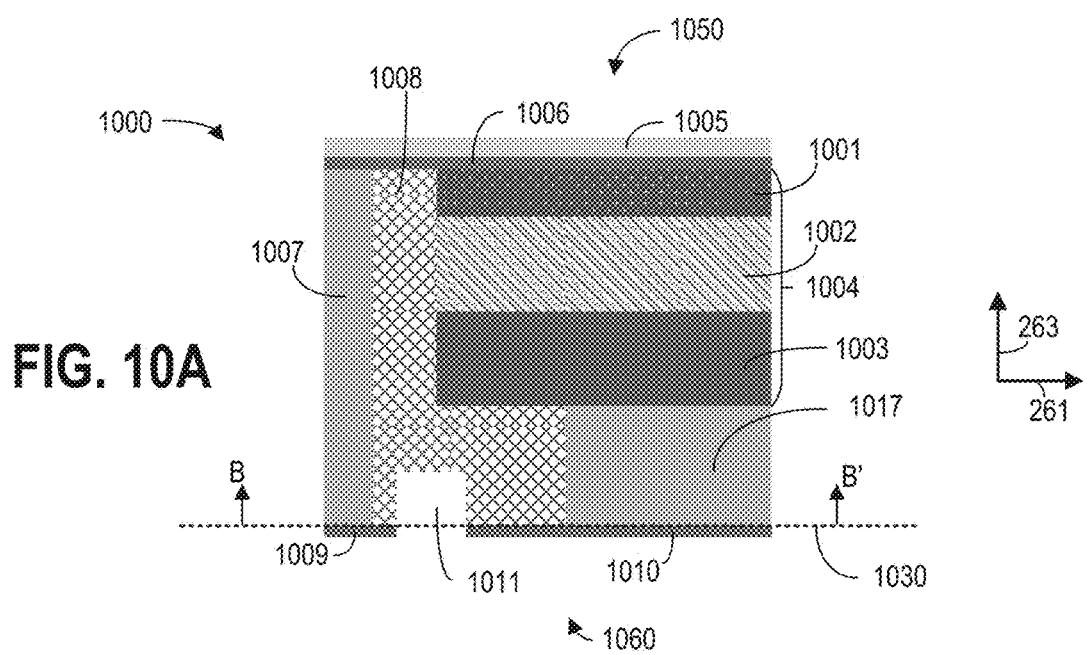
FIG. 10A shows a cross-sectional view of a second embodiment of the transducer.
Figure 10B:
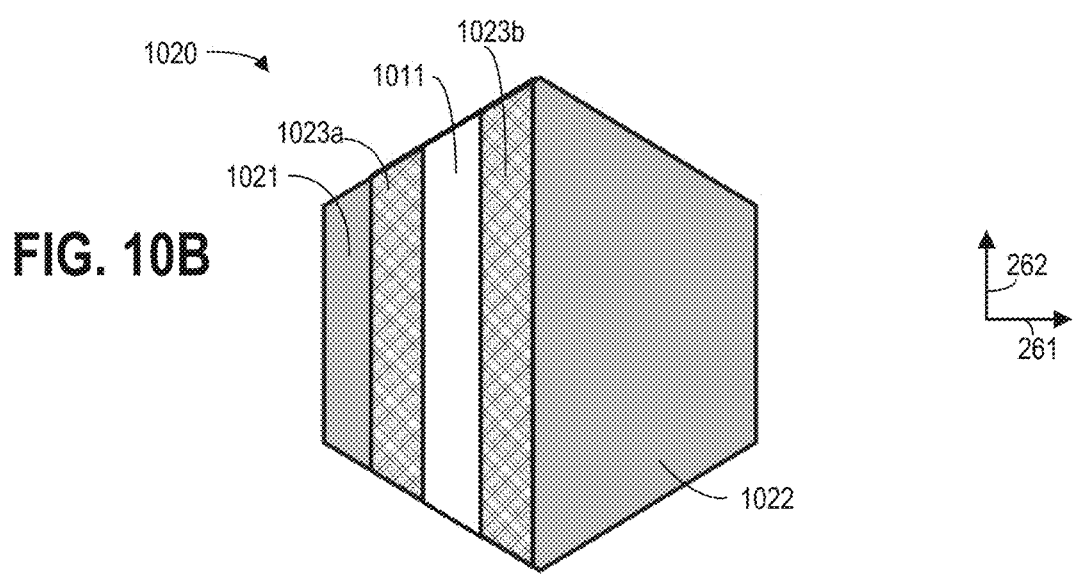
FIG. 10B shows a back surface of the transducer of FIG. 9A.
Figure 11C:
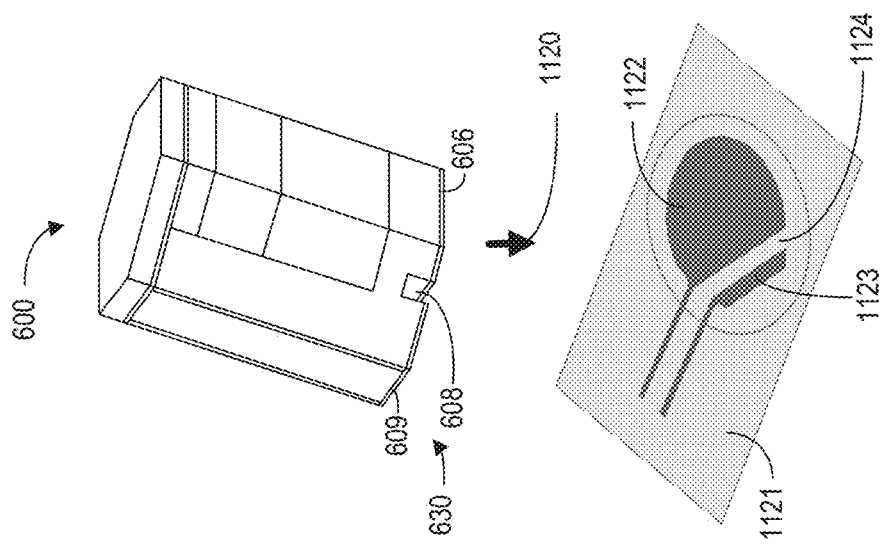
FIG. 11C illustrates the transducer of FIG. 6A surface mounted to a flex pad for a side looking probe.
Figure 11B:
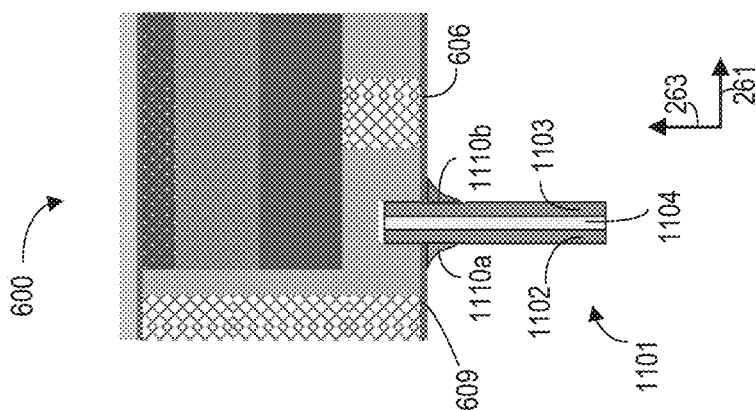
FIG. 11B illustrates a cross-sectional view of the transducer of FIG. 6A with the flex attachment mounted to a back face of the transducer.
Figure 11A:
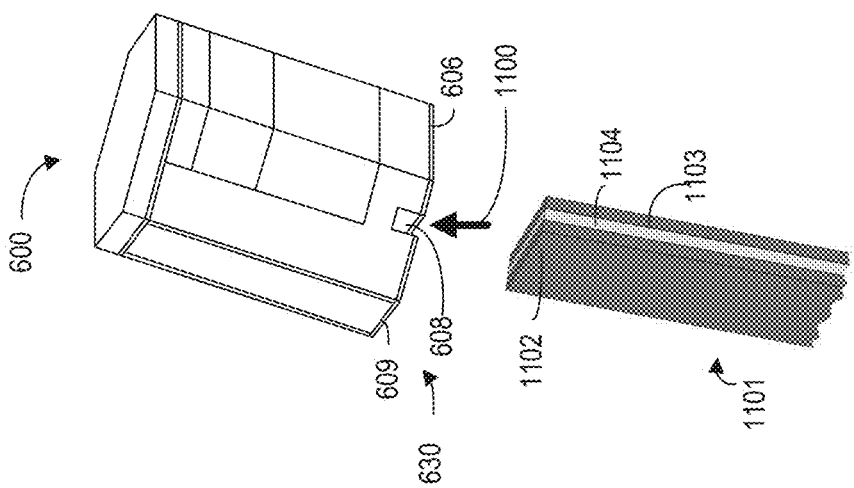
FIG. 11A illustrates the transducer of FIG. 6A mounted to a flex attachment for a forward looking probe.
Figure 12A:
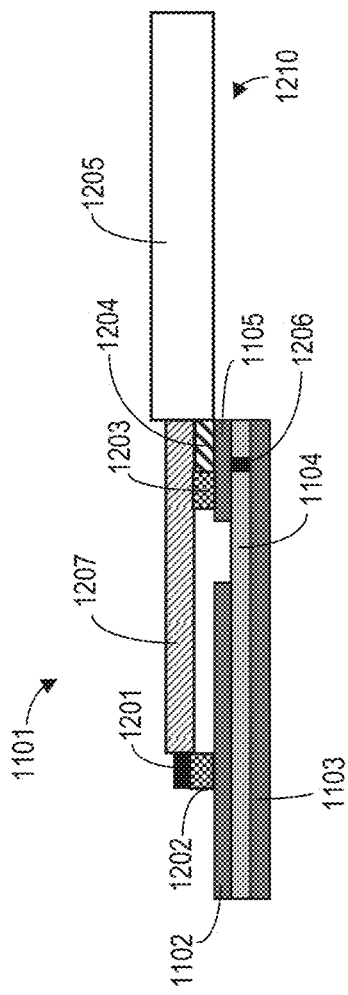
FIG. 12A is a side view of the transducer of FIG. 6A attached to the flex attachment.
Figure 12B:
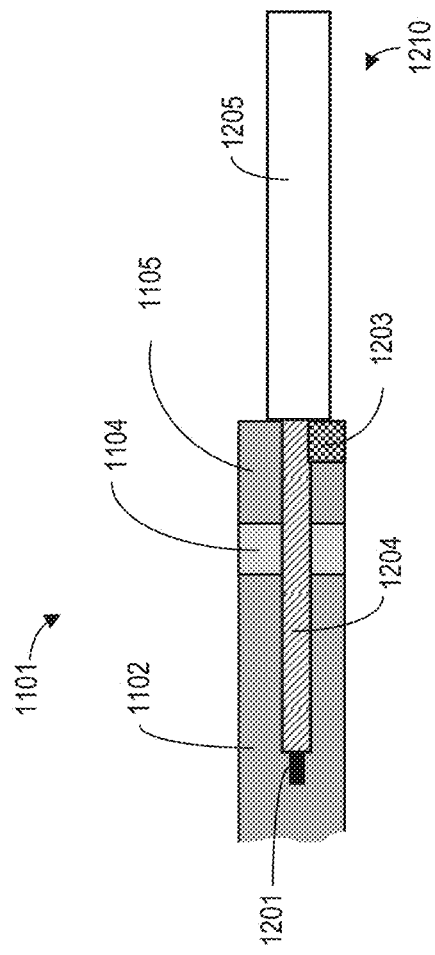
FIG. 12B is a top view of the transducer of FIG. 6A attached to the flex attachment.
Figure 13:
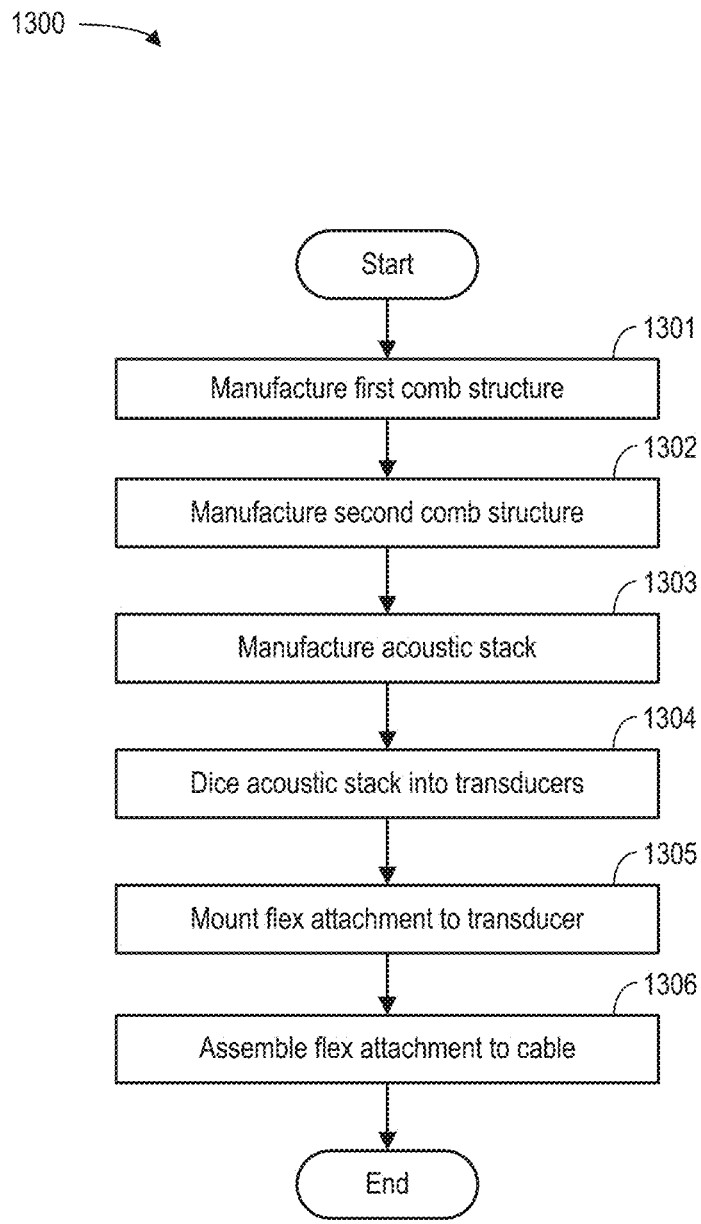
FIG. 13 shows a flow chart for manufacturing a transducer assembly.

The following description relates to various embodiments of a single element transducer. In particular, systems and methods are provided for a single element ultrasound transducer with a wafer level back face attachment for constructing a forward looking or side looking ultrasound probe. FIG. 1 shows an example configuration of the forward looking probe within an ultrasound imaging system. The single element ultrasound transducer is manufactured through wafer level packaging, by dicing through an acoustic stack including interdigitated first comb structure and a second comb structure. Two embodiments of the transducer are presented. The two embodiments of the transducer are manufactured with the same first comb structure, but different second comb structures. In the first embodiment, the second comb structure includes a non-conductive base package and conductive vias. In the second embodiment, the second comb structure includes a conductive base package and non-conductive trench. FIGS. 2A-2D illustrate an example procedure of manufacturing the first and the second comb structures with non-conductive base package. FIG. 3 shows a three dimensional rendering of the second comb structure. FIG. 4 shows the procedure of assembling an acoustic stack based on the first comb structure and the second comb structure with non-conductive base package. Individual transducers may be made by dicing the acoustic stack. FIGS. 5A-5B show an example dicing pattern for a first embodiment of the transducer. The structure of the first embodiment of the transducer is show in FIGS. 6A-6C. FIGS. 7A-7B show another embodiment of the second comb structure with a conductive base package and non-conductive trenches. A procedure for assembling the first comb structure to the second comb structure with conductive base package is shown in FIG. 8. The second embodiment of the transducer may be made by dicing the acoustic stack following lateral dicing lines shown in FIG. 9. The second embodiment of the transducer, which is a negative to the first embodiment, is shown in FIGS. 10A-10B. Both the first and the second embodiments of the transducer have a groove in the back face of the transducer. The groove can receive a distal end of a flex attachment as shown in FIGS. 11A-11B for a forward looking probe. The first and the second embodiments of the transducer may also be surface mounted to a flat flex pad for a side looking probe as shown in FIG. 11C. The proximal end of the flex attachment of FIGS. 11A-11B may couple to a coaxial cable as shown in FIGS. 12A-12B. FIG. 13 is a high level flow chart showing the method of manufacturing the transducer assembly with wafer level back face attachment.

Though a probe with a single element transducer is described by way of example, it should be understood that the present techniques may also be useful for constructing a probe with an array of forward looking single element transducers.

FIG. 1 is a schematic diagram of an ultrasound imaging system 100 in accordance with an embodiment of the invention. System 100 includes a display module 101, a controller/processor 102, a pulser/receiver 103, and a probe 140. The dash lines (110, 120, and 130) indicate communication of electrical signals between system components. A single element ultrasound transducer 105 is mounted at one distal end of cable 104. The transducer 105 faces forward. In other words, the transducer generates and receives reflected acoustic signals in the same direction as the longitudinal axis 107 of the probe. The cable 104 may be a coaxial cable. In an example, the central axis of the coaxial cable may align with the longitudinal axis 107 of the probe. Probe 140 further includes a sheet 106 covering the cable 104 and the transducer 105. The sheet may be flexible and transparent to acoustic signals.

Pulser/receiver 103 is controlled by the controller/processor 102 for generating a high voltage pulse to probe 140. Reflected acoustic signals from an imaged object to the probe are converted into electrical signals and transmitted back to the pulser/receiver via 130. The pulser/receiver may amplify the received electrical signals from the probe. The amplified received electrical signals are further transmitted to controller/processor 102 via dashed line 120. An image or map of the imaged object is constructed based on the received electrical signals. The image or map may be sent to display 101 via dashed line 110 and/or stored in a memory.

In another embodiment, the probe may include an array of ultrasound transducers, and can image or sense a plane or a volume.

FIGS. 2A-2D show a first comb structure and one embodiment of a second comb structure. Each comb structure includes fins and kerfs that are complimentary to each other. The two comb structures may be interdigitally laminated together to form an acoustic stack. In the figures, arrow 261 denotes a horizontal direction. Arrow 263 denotes a vertical direction, perpendicular to the horizontal direction. The lateral direction 262 is perpendicular to both the horizontal and vertical directions.

Figure 2A:
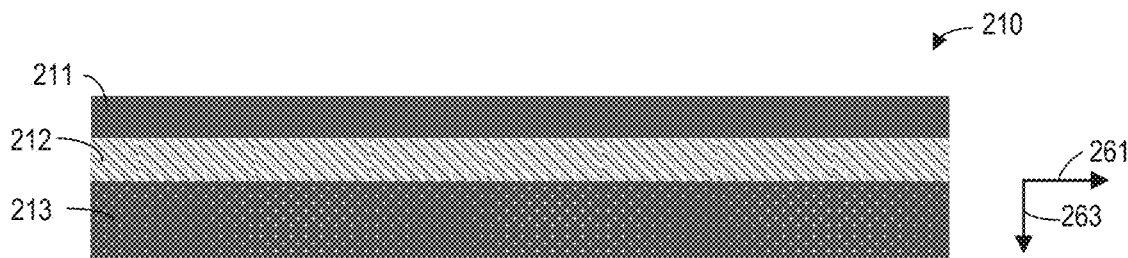
FIG. 2A shows a layered substrate.

FIG. 2A shows a cross-sectional view of a layered substrate 210 including a backing layer 211, a matching layer 213, and a piezoelectric layer 212 intermediate the backing layer and the matching layer. The backing layer, piezoelectric layer, and the matching layer are stacked vertically. The layers may be laminated together using epoxy glue or equivalent.

The piezoelectric layer may be made with a piezoelectric material, such as lead zirconate titanate or any other piezoelectric single crystal. The thickness of the piezoelectric layer may be half of the wavelength of the acoustic signal. The top surface and the bottom surface of the piezoelectric layer act as two electrodes. By applying a voltage across the two electrodes, the piezoelectric material is excited and generates acoustic signals in a direction parallel to the vertical direction. The piezoelectric material may also convert acoustic signals back into electrical signals. When the piezoelectric material is switched from the transmission to the receiving mode, a ringing effect may occur and affect the received signal. The backing layer can dampen the ringing effect. The backing layer may be made of conductive material such as graphite, porous graphite filled with resin, or aluminum. As another example, the thickness of the backing layer may depend on the required acoustic attenuation. In another embodiment, a dematching layer may be positioned between the piezoelectric layer and the backing layer. The dematching layer may be made of tungsten carbide. In yet another embodiment, the backing layer may be replaced with the dematching layer. The matching layer is for matching the acoustic impedance difference between the transducer and the medium that the transducer is immersed within during imaging. As an example, the matching layer may be configured to match the acoustic impedance difference between the transducer and water when the transducer is used for biological tissue imaging. The matching layer may be made of conductive material such as graphite, porous graphite filled with resin, stainless steel, or aluminum.

Figure 2B:
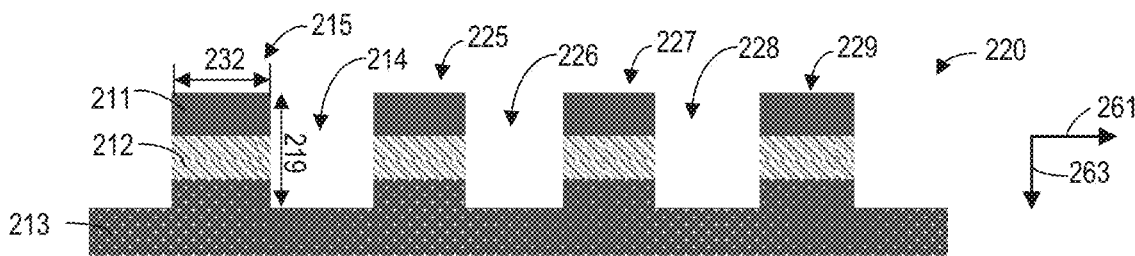
FIG. 2B shows a first comb structure made with the layered substrate.

FIG. 2B shows a cross-sectional view of the first comb structure 220. The first comb structure may be made by dicing the layered substrate 210. For example, the first comb structure 220 may be manufactured by dicing evenly spaced kerfs (214, 226, and 228) into the layered substrate 210. The kerfs are of the same dimensions. The kerfs extend along the lateral direction, and are evenly spaced along the horizontal direction. For example, kerf 214 extends vertically through the backing layer 211 and the piezoelectric layer 212. Kerf 214 further extends into, but not through the matching layer 213. As such, fins (215, 225, 227, and 229) are formed. For example, fin 215 includes the backing layer 211, the piezoelectric layer 212, and part of the matching layer 213. The adjacent fins 215 and 225 are separated by a kerf 214.

Figure 2C:
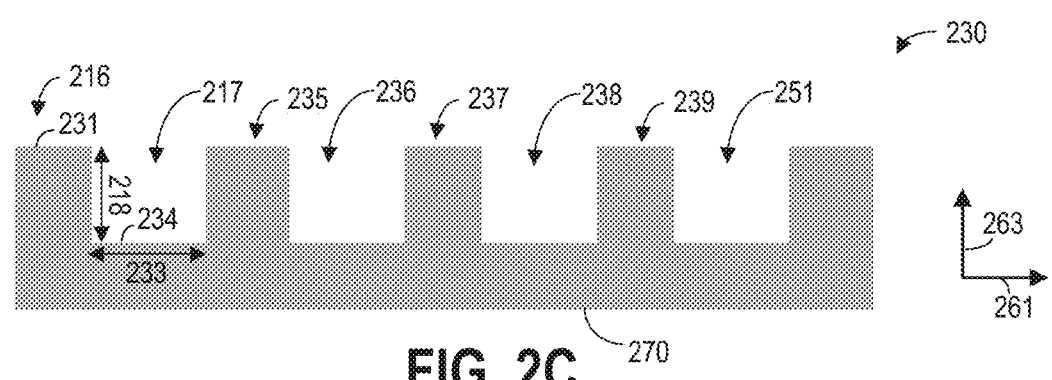
FIG. 2C shows a non-conductive base package.

FIG. 2C shows a non-conductive base package 230. The base package may be made by creating evenly spaced kerfs (217, 236, 238, and 251) along the horizontal axis of a flat non-conductive substrate. The kerfs are of the same dimensions. For example, the substrate may be made with aluminum oxide ($Al_2O_3$) ceramic, polychlorinated biphenyl (PCB), or silicon. The non-conductive base package includes fins (216, 235, 237, and 239) extending laterally. Two adjacent fins, such as fin 217 and fin 235, are separated by a kerf, such as kerf 217. As an example, the base package is complimentary to the first comb structure in a way that the height 218 of fin 216 in the base package is the same as the height 219 of fin 215 in the first comb structure, and width 232 of fin 215 in the first comb structure is less than the width 233 of kerf 217 in the base package. In other words, the respective height of the fins are the same in both the first comb structure and the base package and the respective width of the fins in the first comb structure are less than the respective width of the kerfs in the base package.

Figure 2D:
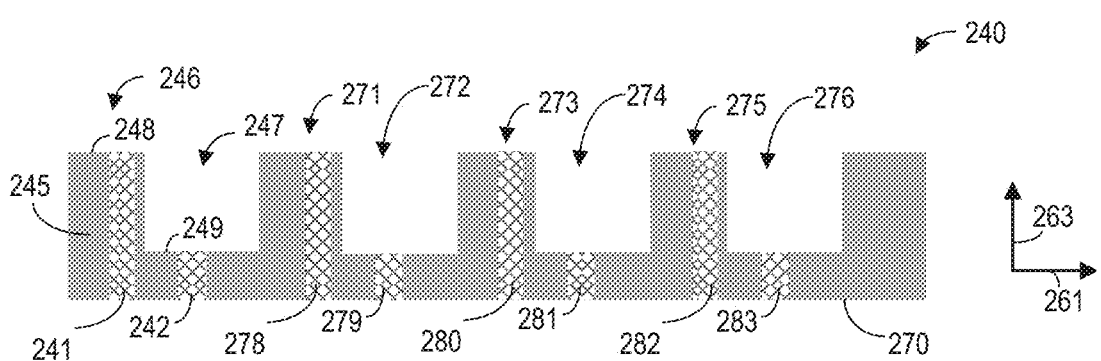
FIG. 2D shows one embodiment of a second comb structure.

FIG. 2D shows a cross-section of a second comb structure 240, which is formed from the base package 230. The second comb structure has fins (246, 271, 273, and 275) and kerfs (247, 272, 274, and 276) complimentary to the fins and kerfs of the first comb structure 220. The second comb structure has vertically conductive vias. The second comb structure may be made by drilling a plurality of first vias (241, 278, 280, and 282) and a plurality of second vias (242, 279, 281, and 283) vertically through the non-conductive base package 230, and filling the vias with conductive material such as tungsten or copper. In one embodiment, the non-conductive base package is made of $Al_2O_3$, while the conductive vias are filled with tungsten. In another embodiment, the non-conductive base package is made of PCB or silicon, and the conductive vias are filled with copper. For example, first via 241 is drilled through fin 216 of the non-conductive base package, from the top surface 231 of fin 216 to the bottom surface 270 of base package 230. The second via 242 is drilled through the bottom surface 234 of kerf 217 to the bottom surface 270 of base package 230. As such, the second comb structure includes alternating first and second vias along the horizontal axis. The entirety of the depth of each of the vias is filled with the conductive material. In other words, in the second comb structure 240, the filling for the first via 241 has a top surface within the same plane of the top surface 248 of fin 246; and the filling for second via 242 has a top surface within the same plane of the bottom surface 249 of kerf 247. In this way, the second comb structure 240 and the first comb structure 220 can be laminated together into an acoustic stack with interdigitated kerfs and fins.

Herein, a top surface of a layer refers to a flat surface extending horizontally and laterally, and is higher than a bottom surface, wherein the increased height in the vertical direction is indicated by arrow 263. The side of a layer refers to a side surface of the layer parallel to the vertical axis.

FIG. 3 shows a three dimensional rendering of the second comb structure 240. As shown in FIG. 3, the vias (e.g., vias 241 and 242) are cylindrical in shape, with a round top surface. However, other via shapes are possible, such as rectangular, oval, etc. The first conductive via 241 is embedded within the fin 246. The top surface of the second conductive via 242 is at the bottom of kerf 247, surrounded by the non-conductive base package 245. Both fin 246 and kerf 247 extend laterally along the entirety of the second comb structure.

FIG. 4 illustrates a procedure of constructing an acoustic stack from the first and second comb structures. Arrow 261 denotes a horizontal direction. Arrow 263 denotes a vertical direction, perpendicular to the horizontal direction. The lateral direction 262 is perpendicular to both the horizontal and vertical directions. Axis 450 indicates time. The time increases as indicated by the arrow.

At T1, the first comb structure 220 is laminated with the second comb structure 240 to form a laminated stack 410. Specifically, the fins of the first comb structure are inserted into the kerfs of the second comb structure, and fins of the second comb structure are inserted into the kerfs of the first comb structure. The two comb structures may be bonded by applying glue in between. As an example, the glue may be non-conducting glue such as epoxy. As another example, the glue may include an anisotropic conductive paste in the vertical direction separating the base package from the matching layer, piezoelectric layer, and the backing layer.

At T2, the laminated stack 410 is ground into ground stack 420. Specifically, the top surface of the laminated stack 410 is ground so that part of the matching layer is removed. As an example, in the ground stack 420, the thickness of the matching layer 213 may be one fourth of the wavelength of the acoustic signal. The matching layer 213 is of the same width in the horizontal direction and same depth in the lateral direction as the piezoelectric layer 212 and the backing layer 211. As such, the top surface of the first via 241 is part of the top surface of ground stack 420. The first via 241 is separated from the piezoelectric layer 212 by base package 245. In another embodiment, the bottom surface of the laminated stack 410 may also be ground to remove part of the base package, in order to adjust the thickness of the transducer to a desired thickness.

At T3, the top surface and the bottom surface of the ground stack 420 are plated with a first conductive coating 431 and a second conductive coating 432, respectively. The coating may be copper, gold, or any type of metal deposition, Further, a second matching layer 433 is deposited on top of the first conductive coating 431. As an example, the second matching layer may be chosen in order to optimize acoustic energy transmission. The second matching layer may have acoustic impedance between 1.5 and 4MRayl. The second matching layer may be electrically conductive or non-conductive.

At T4, an acoustic stack 440 is made by dicing grooves at the bottom of the coated stack 430 with a dicing saw, for example. As shown, groove 441 extends laterally and cuts through the second conductive coating 432, and into but not through the base package 245. Each groove separates a respective first via and second via, such as groove 441 separating first via 241 and second via 242. Each groove is separated from the backing layer 211 by the non-conductive base package 245.

FIGS. 5A and 5B show example patterns for dicing the acoustic stack 440 into individual hexagonal single element transducers. The acoustic stack 440 may be cut along lateral dicing and diagonal dicing lines. FIG. 5A shows an example first lateral dicing line 501 and an example second lateral dicing line 502 in the cross-sectional view of the acoustic stack 440. The first dicing line 501 extends vertically along the first via 241, separating the first via into two parts. The distance 503 between the first dicing line 501 and the second dicing line 502 along the horizontal direction is large enough so that part or all of the second via 242 is within the transducer between dicing line 501 and 502. As another example, the second via 242 and the second dicing line 502 are separated by the base package 245. As yet another example, the second dicing line 502 may be along the side surface 505 of a layered stack 429. The layered stack includes the matching layer 213, the piezoelectric layer 212, and the backing layer 211. FIG. 5B shows example diagonal dicing lines, such as line 504, as well as the lateral dicing lines 501 and 502 in a three dimensional rendering of acoustic stack 440.

In another embodiment, transducers of other shapes may be diced out of the acoustic stack. For example, the acoustic stack may be diced along lateral and horizontal, instead of diagonal, dicing lines into rectangular transducers.

Figure 6A:
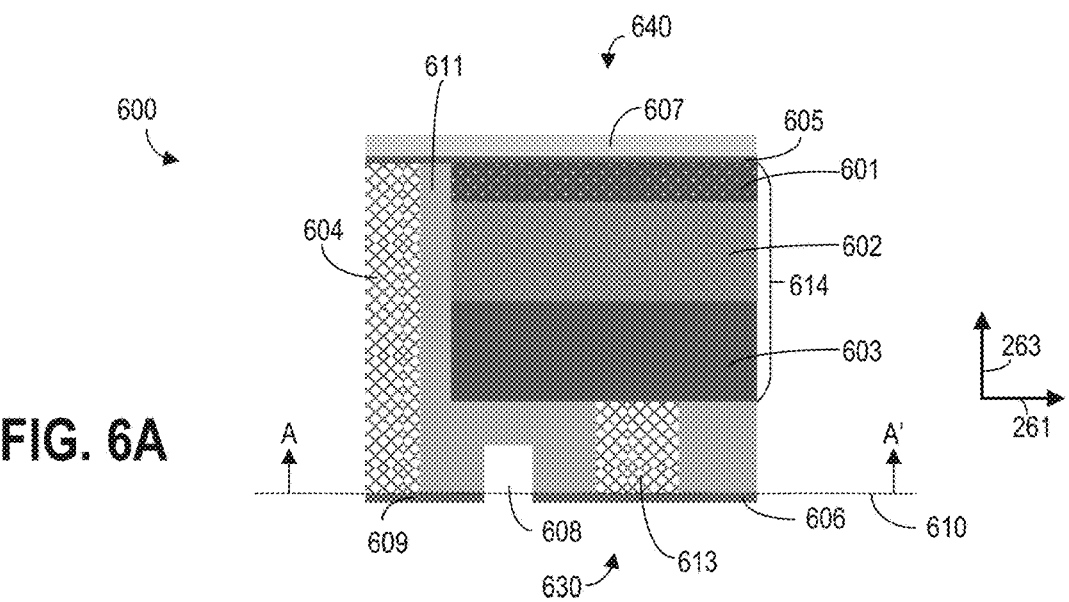
FIG. 6A shows a cross-sectional view of a first embodiment of a transducer.
Figure 6B:
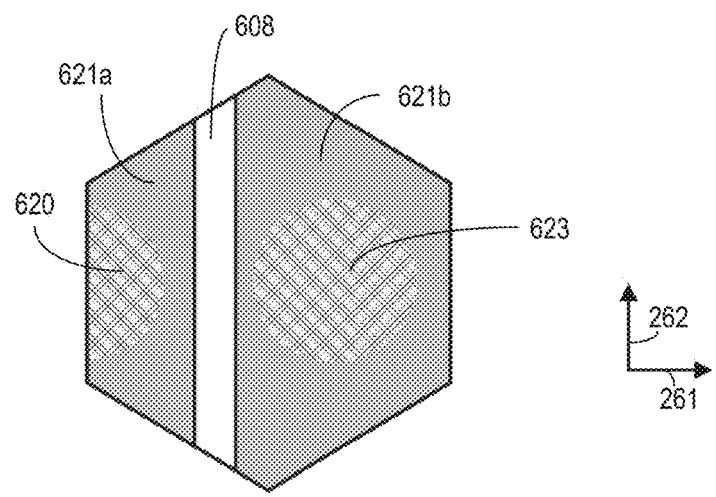
FIG. 6B shows a back surface of the transducer of FIG. 6A.
Figure 6C:
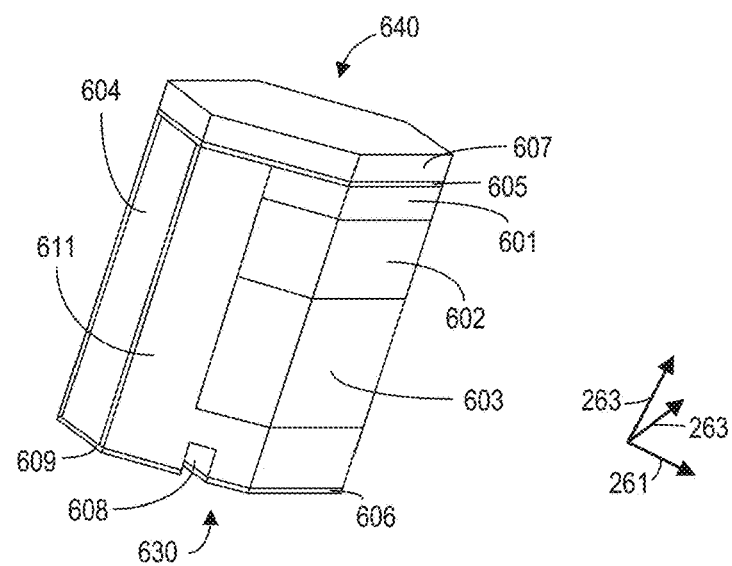
FIG. 6C shows a three dimensional rendering of the transducer of FIG. 6A.

FIGS. 6A-6C show different views of a hexagonal single element ultrasound transducer 600 diced from the acoustic stack 440 as shown in FIGS. 5A-5B. The transducer includes a groove at the back face of the transducer. The groove separates a ground pad and a signal pad of the transducer. A flex attachment may be inserted to the groove for coupling the transducer to a coaxial cable.

FIG. 6A is a cross-sectional view of transducer 600. The transducer includes a layered stack 614 comprising a matching layer 601, a piezoelectric layer 602, and a backing layer 603. The layered stack 614 is separated from a first conductive via 604 by a non-conductive base package 611. The bottom surface of the backing layer 603 is in contact with a second conductive via 613. The top surface of the first conductive via 604, the top surface of the non-conductive base package 611, and the top surface of the matching layer 601 define a front surface of the transducer. A first conductive coating 605 is plated onto the front surface of the transducer. The first conductive coating 605 is between the front surface of the transducer and a second matching layer 607. The second matching layer 607 forms the front face 640 of the transducer. The groove 608 is embedded within the non-conductive base package 611. The bottom surface of the first conductive via 604, the bottom surface of the non-conductive base package 611, and the bottom surface of the second conductive via 613 define a back surface of the transducer. A second conductive coating (such as 432 in FIG. 4) is applied over the back surface. The second conductive coating forms a signal pad 609 and a ground pad 606 separated by groove 608. The bottom surfaces of the ground pad 606 and the signal pad 609 define a back face 630 of the transducer. The back face of the transducer is parallel with the front face of the transducer. The signal pad 609 is in direct contact with the bottom surface of the first via 604. The ground pad 606 is in direct contact with the bottom surface of the second via 613. The first conductive via 604 extends vertically from the signal pad 609 to the first conductive coating 605. The second conductive via 613 extends vertically from the ground pad 606 to the bottom surface of the backing layer 603. As such, the transducer is one solid piece with the signal pad and the ground pad integrated to its body.

The ground pad 606 is electrically coupled with one electrode of the piezoelectric layer 602 via the second conductive via 613 and the backing layer 603. The signal pad 609 is electrically coupled with the other electrode of the piezoelectric layer 602 via the first conductive via 604, the first conductive coating 605, and the matching layer 601. To generate an acoustic signal, a voltage potential may be applied to the transducer by electrically coupling a positive tab of a power source to the signal pad, and a negative (or ground) tab of the power source to the ground pad of the transducer. Alternatively, a voltage potential may be applied to the transducer by electrically coupling a positive tab of the power source to the ground pad of the transducer, and the negative tab (or ground) tab of the power source to the signal pad of the transducer. In other words, the signal and ground pad of the transducer are interchangeable.

FIG. 6B shows the back surface of the transducer, viewed along 610 in a direction A-A'. The back surface includes the bottom surface 620 of the first conductive via 604, the bottom surface (621a and 621b) of the non-conductive base package 611, the bottom surface 623 of the second conductive via 613, and groove 608. The back surface of the transducer is in hexagon shape. The groove 608 separates the bottom surface of the non-conductive base package in two parts 621a and 621b, each part including a bottom surface of one conductive via.

FIG. 6C is a three dimensional rendering of the hexagonal transducer 600. The non-conductive base package 611 partially surrounds the first matching layer 601, piezoelectric layer 602, and the backing layer 603. The first conductive via 604 extends vertically. The front surface of the transducer is formed by the top surfaces of first conductive via 604, the base package 611, and the matching layer 601. The first conductive coating 605 is between the front surface of the transducer and the second matching layer 607. The groove 608 separates the signal pad 609 and the ground pad 606 of the back face of the transducer.

FIGS. 7A-7B show a second embodiment for a second comb structure of the ultrasound transducer. The second comb structure includes a conductive base package with non-conductive trenches.

FIG. 7A is a cross-sectional view of a substrate 710 with non-conductive trenches evenly spaced along the horizontal direction. The substrate 710 may be manufactured by dicing trenches through a conductive base package 711, filling the trenches entirely with non-conductive material, and grinding the top and bottom surface of the substrate. As such, the top surface of the trench 712 is within the same plane as the top surface of the base package 711. The bottom surface of trench 712 is within the same plane as the bottom surface of the base package 711. In one embodiment, the non-conductive trench may be non-conductive resin such as epoxy glue, and the base package may be graphite.

FIG. 7B shows a second comb structure 720 with conductive base package 721. The second comb structure 720 may be made by dicing substrate 710 to form evenly spaced kerfs (723, 728, 731, and 733). For example, in order to form the kerf 723, part of the non-conductive trench 712 is removed as well as part of the conductive base package 711 along the horizontal direction. The bottom surface 727 of the kerf 723 abuts both the non-conductive trench 722 and the conductive base package 721. The second comb structure includes fins (724, 729, 730, and 732) and kerfs complimentary to the fins and kerfs in first comb structure 220 shown in FIG. 2B. Specifically, the heights of the fins in the first comb structure are the same as the heights (e.g., height 726) of the fin in the second comb structure 720. The width (e.g., width 725) of the kerf in the second comb structure 720 are not less than the width of the fins in the first comb structure.

FIG. 8 illustrates a procedure for manufacturing an acoustic stack 880 with the first comb structure 220 and the second comb structure 720. Arrow 261 denotes a horizontal direction. Arrow 263 denotes a vertical direction, perpendicular to the horizontal direction. The lateral direction 262 is perpendicular to both the horizontal and vertical directions. Axis 840 indicates time. The time increases as indicated by the arrow.

At T1, the first comb structure 220 is laminated with the second comb structure 720 to form a laminated stack 860. Specifically, the fins of the first comb structure are inserted into the kerfs of the second negative comb structure, and the fins of the second negative comb structure are inserted into the kerfs of the first comb structure. The two comb structures may be bonded by a glue. As an example, the glue may be non-conducting glue such as epoxy. As another example, the glue may include an anisotropic conductive paste in the vertical direction separating the base package from the matching layer, piezoelectric layer, and the backing layer.

At T2, the laminated stack 860 is ground into ground stack 870. Specifically, the top surface of the laminated stack 860 is ground so that the matching layer 213 is of the same width in the horizontal direction and the same depth in the lateral direction as the piezoelectric layer 212 and the backing layer 211. As an example, thickness of the matching layer 213 may be one fourth of the wavelength of the acoustic signal. As such, the top surface of the non-conductive trench 722 is part of the top surface of ground stack 870. The non-conductive trench 722 is in contact with the side surface of the layered stack including the matching layer 213, the piezoelectric layer 212, and the backing layer 211. The non-conductive trench 722 separates the base package 721 from the piezoelectric layer 212. In another embodiment, the bottom surface of the laminated stack may also be ground to remove part of the base package, in order to adjust the thickness of the transducer to a desired thickness.

At T3, acoustic stack 880 is made. In an example, a first conductive coating 802 may be first plated over the top surface of the ground stack 870, and then a second matching layer 801 is deposited on top of the first conductive coating. The second matching layer may be electrically conductive or non-conductive. A second conductive coating 804 may be plated over the bottom surface of the ground stack 870. Then, grooves are created by dicing through the second conductive coating 804 and into the non-conductive trench 722. An example groove 808 is shown.

The acoustic stack 880 may be diced into individual transducers. FIG. 9 shows example lateral dicing lines for dicing the acoustic stack 880 into individual transducers. As an example, the acoustic stack 880 is diced in the horizontal direction by a first dicing line and a second dicing line. For example, a first dicing line 910 is between the non-conductive trench 722 and the layered stack 901. The layered stack 901 includes the matching layer 213, piezoelectric layer 212, and the backing layer 211. A second dicing line 920 may be along the side surface of the layered stack 901. The first and second dicing lines are on opposite sides of the groove 808.

In one embodiment, the acoustic stack may be diced into hexagonal transducers with lateral dicing lines 910 and 920, and diagonal dicing lines (such as 504 of FIG. 5B). In another embodiment, the acoustic stack may be diced into rectangular transducers with lateral dicing lines 910 and 920, and horizontal dicing lines that are perpendicular to the lateral dicing lines.

FIGS. 10A-10B show one embodiment of a hexagonal transducer 1000 diced out of acoustic stack 880 of FIG. 9. The transducer 1000 is a negative of transducer 600, e.g., in transducer 600, the base package is non-conductive and the vias are conductive; in transducer 1000, the base packages are conductive and the trench is non-conductive. FIG. 10A is a cross-sectional view of the transducer. The first matching layer 1001, piezoelectric layer 1002, and the backing layer 1003 form the layered stack 1004. A non-conductive trench 1008 separates a first conductive base package 1007 and a second conductive base package 1017. The first and second conductive base packages are constructed from base package 721. The bottom surface of the backing layer 1003 is in contact with the non-conductive trench 1008 and the second conductive base package 1017. The top surface of the first conductive base package 1007, the top surface of the non-conductive trench 1008, and the top surface of the first matching layer 1001 define a front surface of the transducer. A first conductive coating 1006 is deposited on top of the front surface, intermediate the front surface and a second matching layer 1005. The top surface of the second matching layer defines a front face 1050 of the transducer. The bottom surface of the first conductive base package 1007, the bottom surface of the non-conductive trench 1008, and the bottom surface of the second conductive base package 1017 define a back surface 1020 of the transducer. A second conductive coating is applied to the back surface. A groove 1011 cuts through the second conductive coating and separates the second conductive coating into a signal pad 1009 and a ground pad 1010. The bottom surfaces of the signal pad and the ground pad define a back face 1060 of the transducer. The back face is parallel to the front face of the transducer. The groove 1011 also cuts into, but not through, the non-conductive trench 1008. Details of the back surface 1020 is shown in FIG. 10B. The signal pad 1009 is in contact with the bottom surface of the first conductive base package 1007. The ground pad 1010 is in contact with the bottom surface of the second conductive base package 1017. The first base package 1007 extends vertically from the signal pad 1009 to the first conductive coating 1006. The second base package 1017 extends vertically from the ground pad 1010 to the bottom surface of the backing layer 1003.

The ground pad 1010 is electrically coupled with the bottom surface of the piezoelectric layer 1002 via the second conductive base package 1017 and the backing layer 1003. The signal pad 1009 is electrically coupled with the top surface of the piezoelectric layer 1002 via the first conductive base package 1007, the first conductive coating 1006, and the first matching layer 1001. As such, when a voltage is applied across the signal pad and the ground pad, the piezoelectric layer 1002 is excited and generates acoustic signals in a direction from the back face 1060 to the front face 1050 of the transducer. A flex attachment may be inserted into the groove 1011 to couple the two electrodes (the signal and ground pads) of the transducer to a coaxial cable.

FIG. 10B shows the back surface 1020 of transducer 1000 viewing from line 1030 in direction B-B'. Groove 1011 separates the bottom surface of the non-conductive trench 1008 into two parts (1023a and 1023b). The groove 1011 and the bottom surface (1023a and 1023b) of the non-conductive trench, insulating the bottom surface 1021 of the first conductive base package 1007 from the bottom surface 1022 of the second conductive base package 1017. The signal pad 1009 covers the bottom surface 1021 of the first conductive base package and the first bottom surface 1023a of the non-conductive trench. The ground pad 1010 covers the bottom surface 1022 of the second conductive base package and the second bottom surface 1023b of the non-conductive trench.

FIG. 11A illustrates a flex attachment 1101 having a distal end configured to be inserted into the groove of the single element ultrasound transducer. As a non-limiting example, the hexagonal transducer 600 is shown here. The flex attachment is inserted into the groove as shown by arrow 1100. The flex attachment includes a non-conductive middle layer 1104 intermediate a first conductive layer 1102 and a second conductive layer 1103. The non-conductive middle layer 1104 may be kapton and the first and second conductive layers may be copper or gold coated copper, at least in one example. By inserting the flex attachment into the groove, the signal pad 609 is in contact with the first conductive layer 1102 and the ground pad 606 is in contact with the second conductive layer 1103. Conductive glue or soldering may be applied to further bond the signal or ground pad with the respective conductive layer. The flex attachment may be a flex PCB. Alternatively, the flex attachment may be of another substrate utilizing surface mounted attachment, such as ASICs and 3DMID. The other distal end of the flex attachment 1101 may be electrically coupled to a processor, such as an imaging system. The other distal end of the flex attachment may be coupled to the processor through a cable, such as a coaxial cable as shown in FIG. 12.

FIG. 11B illustrates a cross-sectional view of the transducer with flex attachment 1101 mounted to its back face. The signal pad 609 of the transducer is in contact with the first conductive layer 1102 of the flex attachment. The ground pad 606 of the transducer is in contact with the second conductive layer 1103 of the flex attachment. Conductive glue or soldering 1110a and 1110b are applied to ensure the signal pad 609 is electrically bonded with the first conductive layer 1102 and the ground pad 606 is electrically bonded with the second conductive layer 1103, respectively.

FIG. 11C illustrates surface mounting the single element transducer to a flat flex pad 1121 for a side looking probe. The flex pad includes circuit printed on one surface of the flex pad. As an example, the flex pad may be polyimide. The circuit may be printed on the flex pad with copper. The circuit may include a signal pad 1123 and a ground pad 1122. The signal pad and the ground pad are separated by non-conductive groove 1124. As indicated by arrow 1120, back face 630 of the transducer may be laminated to the flex pad by aligning the signal pad 609 of the transducer with the signal pad 1123 of the flex pad, aligning the ground pad 606 of the transducer with the ground pad 1122 of the flex pad, and aligning groove 608 of the transducer with the non-conductive groove 1124 of the flex pad.

FIGS. 12A and 12B show the proximal end of the flex attachment 1101 assembled with a coaxial cable 1210. FIG. 12A is a side view of the assembly, and FIG. 12B is a top view of the same assembly. The coaxial cable 1210 includes a jacket 1205, a coaxial ground 1204, and a coaxial signal 1201. The coaxial ground may be insulated from the coaxial signal with a dielectric insulator 1207. The coaxial signal 1201 is bonded to the first conductive layer 1102 of the flex attachment with soldering 1202. Conductive strip 1105 is attached to the non-conductive middle layer 1104, and is on the same side of the first conductive layer 1102 relative to the non-conductive middle layer 1104. The conductive strip may be of the same material as the conductive layers. The coaxial ground 1204 is bonded with the conductive strip 1105 with soldering 1203. The conductive strip 1105 is connected with the second conductive layer 1103 by a conductive via 1206 through the non-conductive middle layer 1104. In this way, the coaxial signal is electrically coupled with the signal pad of the transducer via the first conductive layer of the flex attachment; the coaxial ground is electrically coupled with the ground pad of the transducer via the conductive strip 1105, the conductive via 1206, and the second conductive layer 1103 of the flex attachment. Electrical signals may be sent and received to and from the transducer via the coaxial cable.

FIG. 13 shows an example method 1300 for manufacturing an ultrasound transducer assembly with its back face coupled to a coaxial cable.

At 1301, a first comb structure is manufactured. The first comb structure includes fins and kerfs. The first comb structure may be made by dicing kerfs into a layered substrate including a piezoelectric layer intermediate a matching layer and a backing layer. An example of the first comb structure is shown in FIG. 2B.

At 1302, a second comb structure is manufactured. The second comb structure includes fins and kerfs complimentary to the first comb structure. The second comb structure may be made out of a non-conductive substrate or a conductive substrate. In one embodiment, a non-conductive base package may be made by dicing kerfs into a non-conductive substrate. Then, through vias are drilled into the base package, and filled with conductive material. An example of the second comb structure with non-conductive base package is shown in FIG. 2D. In another embodiment, through trenches may first be cut into a conductive substrate, and filled with non-conductive material. Then, kerfs are cut into the substrate to construct the second comb structure with conductive base package, as shown in FIG. 7B.

At 1303, an acoustic stack is constructed from the first and second comb structures. The first and second comb structures are first laminated together, then ground and plated with conductive coating on the top and bottom surfaces. Further, grooves are cut into the bottom surface of the plated substrate with a dicing saw, for example. The procedures of manufacturing the acoustic stack is shown in FIG. 4.

At 1304, the acoustic stack is diced into individual ultrasound transducers. An example pattern for dicing the acoustic stack with non-conductive base package is shown in FIGS. 5A-5B. Another example of dicing lines for dicing the acoustic stack with conductive base package is shown in FIG. 9.

At 1305, the distal end of a flex attachment is mounted to the back face of the transducer. As an example, FIGS. 11A-11B show a layered flex attachment inserted into the groove of the back face of a hexagonal transducer for constructing a forward looking probe. As another example, a side looking probe may be constructed by surface mounting the back face of a hexagonal transducer onto a flat flex pad with printed circuit printed on top, as shown in FIG. 11C.

At 1306, the other end of the flex attachment is coupled to a cable. For example, FIGS. 12A-12B show an example assembly of the flex PCB with a coaxial cable.

A technical effect of a single element ultrasound transducer with two electrodes integrated into the back end of the transducer is easy attachment to a cable. Another technical effect of the transducers disclosed herein is enabling simple assembly of the transducer with a coaxial cable via a flex attachment including a non-conducive layer intermediate two conductive coating. Another technical effect of the transducer with a wafer level back face attachment is that the electrodes of the transducer may be directly coupled to a coaxial cable with minimal wiring. Another technical effect of the disclosure is that the transducer may be automatically assembled with a coaxial cable, avoiding manually depositing epoxy. Another technical effect of the disclosure is that the transducer may function reliably and robustly.

In one embodiment, an ultrasound transducer comprises a front face, a back face parallel to the front face, the back face having a signal pad, a ground pad, and a groove separating the signal pad from the ground pad, and a piezoelectric layer having a top surface electrically coupled to the signal pad and a bottom surface electrically coupled to the ground pad. In a first example of the embodiment, the ultrasound transducer further comprises a flex attachment having a first conductive layer and a second conductive layer separated by a non-conductive layer, the first conductive layer in contact with the signal pad, the second conductive layer in contact with the ground pad, the piezoelectric layer intermediate a matching layer and a backing layer. A second example of the embodiment optionally includes the first example and further includes, a first conductive via extending vertically from the signal pad to a conductive coating over a top surface of the matching layer, and the signal pad is electrically coupled to the top surface of the piezoelectric layer through the first conductive via, the conductive coating, and the matching layer. A third example of the embodiment optionally includes one or more of the first and second examples, and further includes a second conductive via, and the ground pad is electrically coupled to the bottom surface of the piezoelectric layer through the second conductive via and the backing layer. A fourth example of the embodiment optionally includes one or more of the first through third examples, and further includes, further comprising a non-conductive base package separating the first conductive via from the second conductive via. A fifth example of the embodiment optionally includes one or more of the first through fourth examples, and further includes, the second conductive via is in cylindrical shape and is surrounded by the non-conductive base package. A sixth example of the embodiment optionally includes one or more of the first through fifth examples, and further includes, a first conductive base package extending vertically from the signal pad to a conductive coating over the matching layer, and the signal pad is electrically coupled to the top surface of the piezoelectric layer through the first conductive base package, the conductive coating, and the matching layer. A seventh example of the embodiment optionally includes one or more of the first through sixth examples, and further includes, a second conductive base package extending vertically from the ground pad to the back surface of the backing layer, and the ground pad is electrically coupled to the bottom surface of the piezoelectric layer through the second conductive base package and the backing layer. An eighth example of the embodiment optionally includes one or more of the first through seventh examples, and further includes, a non-conductive trench between the first conductive base package and the second conductive base package. An ninth example of the embodiment optionally includes one or more of the first through eighth examples, and further includes, a flat flex pad with circuit printed on one surface, wherein the back face of the transducer is laminated on top of the flex pad.

In another embodiment, an ultrasound transducer assembly, comprises a piezoelectric layer including a top surface and a bottom surface; a signal pad electrically coupled to the top surface of the piezoelectric layer; and a ground pad electrically coupled to the bottom surface of the piezoelectric layer, the signal pad and the ground pad located in the same plane and separated by a groove, the groove configured to electrically couple the signal pad and the ground pad to a cable. In a first example of the embodiment, the groove is configured to couple the signal pad and ground pad to the cable through a flex attachment having a distal end and a proximal end, the distal end inserted into the groove and the proximal end coupled to the cable. A second example of the embodiment optionally includes the first example and further includes, the flex attachment has a first conductive layer in contact with the signal pad and a second conductive layer in contact with the ground pad, and the first conductive layer is insulated from the second conductive layer by a non-conductive layer. A third example of the embodiment optionally includes one or more of the first and second examples, and further includes, a backing layer having a top surface in contact with the bottom surface of the piezoelectric layer; and a matching layer having a top surface and a bottom surface, the top surface of the matching layer plated with a conductive coating, the bottom surface of the matching layer in contact with the top surface of the piezoelectric layer. A fourth example of the embodiment optionally includes one or more of the first through third examples, and further includes, a conductive via extending vertically from the conductive coating to the signal pad, and a non-conductive base package between the conductive via and the piezoelectric layer. A fifth example of the embodiment optionally includes one or more of the first through fourth examples, and further includes, a first conductive base package extending vertically from the conductive coating to the signal pad, and a non-conductive trench between the first conductive base package and the piezoelectric layer. A sixth example of the embodiment optionally includes one or more of the first through fifth examples, and further includes, a second conductive base package coupled between the backing layer and the ground pad, the second base package separated from the first base package by the non-conductive trench.

In another embodiment, a method comprises laminating a first comb structure and a second comb structure into an acoustic stack, the first comb structure having fins including a piezoelectric layer intermediate a matching layer and a backing layer, the second comb structure having fins and kerfs; plating a first conductive layer over a top surface of the acoustic stack; plating a second conductive layer over a bottom surface of the acoustic stack; cutting a groove through the second conductive layer; dicing the cut acoustic stack into an ultrasound transducer having a back face including a signal pad and a ground pad separated by the groove; and inserting a distal distal end of a flex attachment into the groove, the flex attachment having a proximal end configured to electrically couple to a processor. In a first example of the embodiment, the method further includes manufacturing the second comb structure by forming conductive vias in a non-conductive substrate. A second example of the embodiment optionally includes the first example and further includes manufacturing the second comb structure by forming a non-conductive trench in a conductive substrate.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method, comprising:
   laminating a first comb structure and a second comb structure into an acoustic stack, the first comb structure having fins including a piezoelectric layer intermediate a matching layer and a backing layer, the second comb structure having fins and kerfs;
   plating a first conductive layer over a top surface of the acoustic stack;
   plating a second conductive layer over a bottom surface of the acoustic stack;
   cutting a groove through the second conductive layer;
   dicing the cut acoustic stack into an ultrasound transducer having a back face including a signal pad and a ground pad formed by the second conductive layer and separated by the groove; and
   inserting a distal end of a flex attachment into the groove, the flex attachment having a proximal end configured to electrically couple to a processor, wherein the flex attachment includes a non-conductive middle layer intermediate a first conductive layer and a second conductive layer.

2. The method of claim 1, further comprising manufacturing the second comb structure by forming conductive vias in a non-conductive substrate.

3. A method, comprising:
   laminating a first comb structure and a second comb structure into an acoustic stack, the first comb structure having fins including a piezoelectric layer intermediate a matching layer and a backing layer, the second comb structure having fins and kerfs;
   manufacturing the second comb structure by forming a non-conductive trench in a conductive substrate;
   plating a first conductive layer over a top surface of the acoustic stack;
   plating a second conductive layer over a bottom surface of the acoustic stack;
   cutting a groove through the second conductive layer;
   dicing the cut acoustic stack into an ultrasound transducer having a back face including a signal pad and a ground pad formed by the second conductive layer and separated by the groove; and
   inserting a distal end of a flex attachment into the groove, the flex attachment having a proximal end configured to electrically couple to a processor.

4. The method of claim 1, wherein the non-conductive middle layer is kapton and the first and second conductive layers are copper or gold coated copper.

5. The method of claim 1, wherein by inserting the flex attachment into the groove, the signal pad is in contact with the first conductive layer and the ground pad is in contact with the second conductive layer.

6. The method of claim 5, further comprising applying conductive glue or soldering to further bond the signal pad with the first conductive layer.

7. The method of claim 5, further comprising applying conductive glue or soldering to further bond the ground pad with the second conductive layer.

8. The method of claim 1, wherein the flex attachment is a flex PCB.

9. The method of claim 1, wherein the proximal end of the flex attachment is configured to electrically couple to the processor through a cable.

10. The method of claim 9, wherein the cable is a coaxial cable.

11. The method of claim 3, wherein the flex attachment includes a non-conductive middle layer intermediate a first conductive layer and a second conductive layer.

12. The method of claim 11, wherein the non-conductive middle layer is kapton and the first and second conductive layers are copper or gold coated copper.

13. The method of claim 3, wherein by inserting the flex attachment into the groove, the signal pad is in contact with the first conductive layer and the ground pad is in contact with the second conductive layer.

14. The method of claim 13, further comprising applying conductive glue or soldering to further bond the signal pad with the first conductive layer.

15. The method of claim 13, further comprising applying conductive glue or soldering to further bond the ground pad with the second conductive layer.

16. The method of claim 3, wherein the flex attachment is a flex PCB.

17. The method of claim 3, wherein the proximal end of the flex attachment is configured to electrically couple to the processor through a cable.

18. The method of claim 17, wherein the cable is a coaxial cable.

* * * * *